(12) United States Patent
Ravaud et al.

(10) Patent No.: US 9,913,786 B2
(45) Date of Patent: Mar. 13, 2018

(54) MOISTURIZING COMPOSITION WHICH MAY BE APPLIED TO WET SKIN IN THE FORM OF AN OIL-IN-WATER EMULSION; MOISTURIZING CARE PROCESS

(71) Applicant: L'OREAL, Paris (FR)

(72) Inventors: Magali Ravaud, Paris (FR); Matthieu Cassier, Saint Cloud (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 14/913,830

(22) PCT Filed: Aug. 21, 2014

(86) PCT No.: PCT/EP2014/067809
§ 371 (c)(1),
(2) Date: Feb. 23, 2016

(87) PCT Pub. No.: WO2015/028381
PCT Pub. Date: Mar. 5, 2015

(65) Prior Publication Data
US 2016/0206531 A1    Jul. 21, 2016

(30) Foreign Application Priority Data

Aug. 29, 2013 (FR) ..................................... 13 58254

(51) Int. Cl.
| | |
|---|---|
| *A61K 47/00* | (2006.01) |
| *A61K 8/31* | (2006.01) |
| *A61K 8/37* | (2006.01) |
| *A61K 8/39* | (2006.01) |
| *A61K 8/73* | (2006.01) |
| *A61Q 19/00* | (2006.01) |
| *A61K 8/86* | (2006.01) |
| *A61K 8/92* | (2006.01) |
| *A61K 8/06* | (2006.01) |

(52) U.S. Cl.
CPC ................ *A61K 8/31* (2013.01); *A61K 8/062* (2013.01); *A61K 8/375* (2013.01); *A61K 8/39* (2013.01); *A61K 8/732* (2013.01); *A61K 8/86* (2013.01); *A61K 8/922* (2013.01); *A61Q 19/00* (2013.01); *A61K 2800/592* (2013.01); *A61K 2800/5922* (2013.01)

(58) Field of Classification Search
USPC ........................................................ 514/778
See application file for complete search history.

(56) References Cited

U.S. PATENT DOCUMENTS

| | | | | |
|---|---|---|---|---|
| 7,138,128 | B2 * | 11/2006 | Bleckmann | ......... B01F 17/0028 424/401 |
| 2005/0037036 | A1 | 2/2005 | Nielsen et al. | |
| 2006/0233721 | A1 * | 10/2006 | Tamarkin | ............... A61K 8/046 424/47 |
| 2008/0299200 | A1 * | 12/2008 | Leser | .................. B01F 17/0028 424/484 |

FOREIGN PATENT DOCUMENTS

| | | |
|---|---|---|
| CN | 101410172 A | 4/2009 |
| CN | 102448422 A | 5/2012 |
| EP | 1676563 A1 | 7/2006 |
| EP | 2095808 A1 | 9/2009 |
| EP | 2100585 A1 | 9/2009 |
| EP | 2255849 A2 | 12/2010 |
| FR | 2794997 A1 | 12/2000 |
| WO | WO-00/56270 A2 | 9/2000 |
| WO | WO-03/013460 A2 | 2/2003 |

* cited by examiner

*Primary Examiner* — Rei Tsang Shiao
(74) *Attorney, Agent, or Firm* — Polsinelli PC

(57) ABSTRACT

The present invention relates to a composition in the form of an oil-in-water emulsion, comprising, in a physiologically acceptable medium:
a) at least one aqueous phase; and
b) at least one oily phase comprising at least one apolar non-volatile hydrocarbon-based oil and at least one pasty apolar lipophilic hydrocarbon-based compound; and
c) at least one hydrophilic gelling polysaccharide; and
d) at least one mixture of emulsifying nonionic surfactants comprising (i) at least one fatty acid ester of polyol and (ii) at least one polyalkylene glycol ester.

The present invention also relates to a cosmetic care process for moisturizing a human keratin material, in particular the skin, characterized in that it comprises the application to the surface of the said keratin material of a composition as defined previously.

The present invention more particularly relates to a cosmetic care process for moisturizing a human keratin material, in particular the skin, on contact with water (for example under the shower or in the bath), characterized in that it comprises the application to the surface of the said human keratin material of a composition as defined previously, followed by rinsing with water and wiping.

20 Claims, No Drawings

MOISTURIZING COMPOSITION WHICH MAY BE APPLIED TO WET SKIN IN THE FORM OF AN OIL-IN-WATER EMULSION; MOISTURIZING CARE PROCESS

CROSS REFERENCE TO RELATED APPLICATIONS

This application is a National Phase filing under 35 U.S.C. § 371 of PCT/EP2014/067809 filed on Aug. 21, 2014; and this application claims priority to Application No. 1358254 filed in France on Aug. 29, 2013 under 35 U.S.C. § 119. The entire contents of each application are hereby incorporated by reference.

The present invention relates to a composition in the form of an oil-in-water emulsion, comprising, in a physiologically acceptable medium:
 a) at least one aqueous phase; and
 b) at least one oily phase comprising at least one apolar non-volatile hydrocarbon-based oil and at least one pasty apolar lipophilic hydrocarbon-based compound; and
 c) at least one hydrophilic gelling polysaccharide; and
 d) at least one mixture of emulsifying nonionic surfactants comprising (i) at least one fatty acid ester of polyol and (ii) at least one polyalkylenes glycol ester.

The present invention also relates to a cosmetic care process for moisturizing a human keratin material, in particular the skin, characterized in that it comprises the application to the surface of the said keratin material of a composition as defined previously.

Many cosmetic compositions are known for moisturizing the skin. It is common practice to moisturize with a body milk of the oil-in-water emulsion type. It is generally necessary to wait until the formula has penetrated and dried before getting dressed, otherwise the skin remains tacky.

There is a need for new compositions that have good moisturizing efficacy, which may be applied to wet skin especially under the shower or in the bath, and which may be rinsed off easily, leaving, after wiping and drying on the skin, a water-resistant film that makes it possible to obtain a soft, slightly tacky and sparingly greasy feel, which makes it possible to get dressed quickly and to obtain, after 24 hours, a sensation of well-moisturized skin. These compositions must also be stable under storage conditions, especially after two months at room temperature (20-25° C.) and after two months at 45° C. and without any drop in pH or loss of viscosity.

Moisturizing milks that may be applied to wet skin are known on the market, such as the product Olay Body®—"Quench In-Shower Body Lotion" comprising the following ingredients: water, petrolatum, mineral oil, hydroxypropyl starch phosphate, fragrance, stearyl alcohol, mica, polysorbate 60, titanium dioxide, DMDM hydantoin, cetyl alcohol, triethoxycaprylylsilane, disodium EDTA, phenoxyethanol iodopropynyl butylcarbamate, tin oxide. This type of composition has, firstly, the drawback of producing after application a deposit of thick, water-resistant film which gives a sensation of tacky skin, requiring a waiting time before getting dressed that is similar to that of a body milk applied to unmoistened skin. Secondly, this type of formulation contains as emulsifying surfactant Polysorbate-60 (or oxyethylenated (20 OE) sorbitan monostearate), which may lead to problems of stability on storage, reflected by phase separation of the emulsion and/or a drop in pH and/or a loss of viscosity.

A moisturizing milk that may be applied to wet skin is also known, such as the product Nivea®—"Under the Shower Body Balm Nutritive" comprising the following ingredients: water, microcrystalline wax, liquid paraffin, glycerol, cetearyl alcohol, hydrogenated cocoyl glycerides, stearyl alcohol, myristyl alcohol, sea salt, sodium carbomer, sodium acrylates/C10-30 alkyl acrylate crosspolymer, aluminium starch octenylsuccinate, phenoxyethanol, methylisothiazolinone, linalool, limonene, butylphenyl methylpropional. This type of composition has, firstly, the drawback of producing after application a deposit of thick, water-resistant film which gives a sensation of tacky skin, requiring a waiting time before getting dressed that is similar to that of a body milk applied to unmoistened skin.

The Applicant has discovered, surprisingly, that a composition in the form of an oil-in-water emulsion comprising, in a physiologically acceptable medium:
 a) at least one aqueous phase; and
 b) at least one oily phase comprising at least one apolar non-volatile hydrocarbon-based oil and at least one pasty apolar lipophilic hydrocarbon-based compound; and
 c) at least one hydrophilic gelling polysaccharide; and
 d) at least one mixture of nonionic surfactants comprising (i) at least one fatty acid ester of polyol and (ii) at least one polyalkylene glycol ester, can be applied to wet skin, leaving, after wiping and drying, a water-resistant film that is substantially less greasy and less tacky than the moisturizing milks used under the shower that are known from the prior art. This same composition also makes it possible to obtain, after 24 hours, skin that is well moisturized. The Applicant has found that this same composition has good stability on storage, especially after two months at room temperature (20-25° C.) and after two months at 45° C. and without any drop in pH or loss of viscosity.

This discovery forms the basis of the invention.

The present invention relates to a composition in the form of an oil-in-water emulsion, comprising, in a physiologically acceptable medium:
 a) at least one aqueous phase; and
 b) at least one oily phase comprising at least one apolar non-volatile hydrocarbon-based oil and at least one pasty apolar lipophilic hydrocarbon-based compound; and
 c) at least one hydrophilic gelling polysaccharide; and
 d) at least one mixture of emulsifying nonionic surfactants comprising (i) at least one fatty acid ester of polyol and (ii) at least one polyalkylenes glycol ester.

The present invention also relates to a cosmetic care process for moisturizing a human keratin material, in particular the skin, characterized in that it comprises the application to the surface of the said keratin material of a composition as defined previously.

The present invention more particularly relates to a cosmetic care process for moisturizing a human keratin material, in particular the skin, on contact with water (for example under the shower or in the bath), characterized in that it comprises the application to the surface of the said human keratin material of a composition as defined previously, followed by rinsing with water and wiping.

Other characteristics, aspects and advantages of the invention will emerge on reading the detailed description that follows.

The term "human keratin material" means the skin (of the body, face and around the eyes), hair, eyelashes, eyebrows, bodily hair, nails, lips or mucous membranes.

The term "physiologically acceptable medium" means any medium that is compatible with the skin and/or its integuments, which has a pleasant colour, odour and feel, and which does not cause any unacceptable discomfort (stinging, tautness or redness) liable to discourage the consumer from using this composition. A physiologically acceptable medium is preferentially a cosmetically or dermatologically acceptable medium.

For the purposes of the present patent application, the term "hydrophilic gelling polysaccharide" means a polysaccharide compound that is capable of gelling the aqueous phase of the compositions according to the invention. The gelling agent is hydrophilic and is thus present in the aqueous phase of the composition. The gelling agent may be water-soluble or water-dispersible in the said aqueous phase.

The term "emulsion" means any macroscopically homogeneous, kinetically stable composition comprising at least two mutually immiscible phases; one being a dispersing continuous phase and the other being dispersed in the said continuous phase in the form of droplets. The two phases are kinetically stabilized by at least one emulsifying system generally comprising at least one emulsifying surfactant.

The term "oil-in-water emulsion" means a composition consisting of an aqueous dispersing continuous phase and an oily dispersed discontinuous phase.

The term "nonionic surfactant" means any surfactant having a nonionic hydrophilic part and a lipophilic part.

The term "emulsifying surfactant" refers to any surfactant compound or mixture of surfactant compounds that is capable of increasing the kinetic stability of an emulsion. These compounds are generally amphiphilic and are surfactants characterized by their more or less hydrophilic or more or less lipophilic nature which will determine their ability to stabilize direct emulsions or inverse emulsions. They are especially classified by their HLB according to the calculation method of W. C. Griffin in the document "Classification of Surface Active Agents by HLB, Journal of the Society of Cosmetic Chemists 1 (1949) 311" and in the document "Calculation of HLB of Non Ionic Surfactants, Journal of the Society of Cosmetic Chemists 5 (1954) 249". The calculation of the HLB according to this calculation method is performed according to the equation:

$$HLB = 20 \times M_h / M$$

where $M_h$ is the molar mass of the hydrophilic part of the surfactant and M is the total molecular mass of the molecule.

Aqueous Phase

The aqueous phase of the emulsions or compositions of the invention contains water and optionally other water-soluble or water-miscible organic solvents.

The aqueous phase of the emulsions is preferably present in a composition of the invention in a content ranging from 30% to 70% by weight and in particular from 32% to 60% by weight relative to the total weight of the said composition.

An aqueous phase that is suitable for use in the invention may comprise, for example, a water chosen from a natural spring water, such as water from La Roche-Posay, water from Vittel or waters from Vichy, or a floral water.

The water-soluble or water-miscible solvents that are suitable for use in the invention comprise short-chain monoalcohols, for example $C_1$-$C_4$ monoalcohols, such as ethanol or isopropanol; diols or polyols, such as ethylene glycol, 1,2-propylene glycol, 1,3-butylene glycol, hexylene glycol, diethylene glycol, dipropylene glycol, 2-ethoxyethanol, diethylene glycol monomethyl ether, triethylene glycol monomethyl ether, glycerol and sorbitol, and mixtures thereof.

According to a preferred embodiment, use may more particularly be made of propylene glycol, glycerol or sorbitol, and mixtures thereof.

A water-soluble organic solvent may be present in a composition of the invention in a content ranging from 1% to 30% by weight and in particular from 2% to 20% by weight relative to the total weight of the said composition.

Mixture of Nonionic Surfactants

The compositions according to the invention comprise a mixture of nonionic surfactants comprising (i) at least one fatty acid ester of polyol and (ii) at least one fatty acid ester of polyalkylene glycol, and mixtures thereof.

a) Fatty Acid Ester of Polyalkylene Glycol

The fatty acid esters of polyalkylene glycol that are suitable for use in the invention are preferably chosen from esters of a polyalkylene glycol and of a $C_8$-$C_{24}$, in particular $C_{10}$-$C_{22}$, more particularly $C_{12}$-$C_{20}$ and more preferably $C_{14}$-$C_{18}$ fatty acid. Advantageously, the fatty acid esters of polyalkylene glycol are chosen from esters of polyalkylene glycol and of a $C_{12}$-$C_{22}$ fatty acid.

The fatty acid may be linear or branched, and saturated or unsaturated.

As examples of fatty acid esters of polyalkylene glycol that are suitable for use in the invention, mention may be made of esters of polyalkylene glycol and of a fatty acid chosen from capric acid, lauric acid, myristic acid, palmitic acid, stearic acid, isostearic acid, arachidic acid, behenic acid, palmitoleic acid, oleic acid, linoleic acid, arachidonic acid and erucic acid. An example of a C16-C20 fatty acid polymer that may be mentioned is poly(12-hydroxystearic acid).

Preferably, a fatty acid may be chosen from lauric acid, stearic acid, behenic acid, arachidic acid and palmitic acid, and mixtures thereof.

The polyalkylene glycol blocks that are suitable for use in the invention may advantageously be polyethylene glycol or polypropylene glycol blocks, or combinations thereof, and are preferably polyethylene glycol blocks, comprising from 1 to 100 units, especially from 2 to 50 units, preferably from 4 to 40 units, more preferably from 6 to 30 units and more preferentially from 40 to 100 units of alkylene oxide.

According to a preferred embodiment, the fatty acid esters of polyalkylene glycol that may be used according to the invention are esters formed from 1 to 100, or even from 2 to 75, or even from 3 to 50, and preferably from 4 to 40 ethylene oxide units and from at least one fatty acid chain comprising from 12 to 22 carbon atoms.

As examples of ethoxylated fatty esters that are particularly suitable for use in the invention, mention may be made of the stearic acid ester comprising 40 ethylene oxide units, such as the product sold under the name Myrj 52® (CTFA name: PEG-40 stearate) by the company ICI, or the behenic acid ester comprising 8 ethylene oxide units (CTFA name: PEG-8 behenate), such as the product sold under the name Compritol HD5 ATO® by the company Gattefossé, or PEG-8 isostearate such as the product sold under the name Prisorine 3644® by the company Uniqema, and mixtures thereof.

b) Fatty Acid Ester of Polyol

According to the invention, the term "fatty acid ester of polyol" means an ester of polyol and of fatty acid or of fatty acid polymer in which the fatty acid or the fatty acid polymer comprises at least one carboxylic function and at least one $C_7$-$C_{23}$ alkyl chain, and the polyol is chosen from glycerol, a polyglycerol and sorbitan, and mixtures thereof.

A fatty acid ester of polyol may be a polyester, and preferably a fatty acid diester of polyol.

A fatty acid ester of polyol that is suitable for use in the invention may preferably be chosen from esters of a polyol and of a fatty acid or a fatty acid polymer, and preferably a $C_8$-$C_{24}$, in particular $C_{10}$-$C_{22}$, more particularly $C_{12}$-$C_{20}$ and more preferably $C_{14}$-$C_{18}$ fatty acid.

The fatty acid may be linear or branched, and saturated or unsaturated.

According to one embodiment, the fatty acid may be a dicarboxylic acid containing from 10 to 16 carbon atoms, such as sebacic acid or dodecanedioic acid.

As examples of fatty acid esters of polyol that are suitable for use in the invention, mention may be made of esters of polyol and of a fatty acid chosen from capric acid, lauric acid, myristic acid, palmitic acid, stearic acid, isostearic acid, arachidic acid, behenic acid, palmitoleic acid, oleic acid, linoleic acid, arachidonic acid and erucic acid. Preferably, the fatty acid is stearic acid or isostearic acid.

An example of a $C_{16}$-$C_{20}$ fatty acid polymer that may be mentioned is poly(12-hydroxystearic acid).

According to a particular embodiment, the fatty acid ester of polyol is chosen from esters of glycerol or of polyglycerol and of a $C_8$-$C_{24}$ and preferably $C_{16}$-$C_{20}$ fatty acid.

The term "polyglycerol" means a compound having the following general formula:

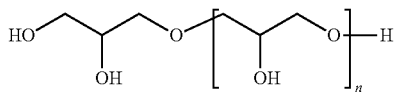

in which the degree of condensation n ranges from 1 to 11, preferably from 2 to 9 and even more preferentially from 3 to 5.

As fatty acid esters of polyglycerol that are preferred according to the invention, mention may be made especially of: glyceryl stearate citrate (and) polyglyceryl-3 stearate (and) hydrogenated lecithin sold under the name Heliofeel® by Lucas Meyer, polyglyceryl-3 methylglucose distearate sold under the name Tego Care 450® by Evonik Goldschmidt, glyceryl stearate SE sold under the name Tegin Pellets® by the company Evonik Goldschmidt, and mixtures thereof.

As examples of fatty acid esters of polyol that may be used in the invention, mention may be made of esters of polyol and of stearic acid, and mixtures thereof, in particular isostearic acid esters of glycerol, for instance Glyceryl Cocoate/Citrate/Lactate (and) Glyceryl Isostearate sold under the name Imwitor 390® by the company Sasol.

Use will be made more particularly of a mixture of glyceryl monostearate and PEG-100 stearate (INCI name: Glyceryl Stearate (and) PEG-100 Stearate) such as the product sold under the trade name Arlacel 165® by the company Croda, under the trade name Simulsol 165® by the company SEPPIC or under the trade name Tego Care C180® by the company Evonik Goldschmidt.

Preferentially, the mixture of nonionic surfactants is present in an active material content ranging from 0.2% to 6% by weight, preferably from 0.4% to 5% by weight, better still from 0.5% to 4% by weight and even better still from 0.8% to 4% by weight relative to the total weight of the composition.

Additional Emulsifying Surfactants

The emulsions in accordance with the invention may also contain at least one additional emulsifying surfactant and preferably at least one additional nonionic emulsifying surfactant.

According to a particular form of the invention, the compositions of the invention comprise at least one fatty alcohol that is preferably $C_{10}$-$C_{22}$ and more preferentially $C_{16}$-$C_{22}$.

The term "fatty alcohol" means any non-alkoxylated alcohol comprising a linear saturated hydrocarbon-based chain, in particular consisting of a linear alkyl chain, the said chain comprising at least 10 carbon atoms and a hydroxyl function.

The term "hydrocarbon-based chain" means an organic group predominantly consisting of hydrogen atoms and carbon atoms.

Preferentially, the additional emulsifying surfactant(s) are present in an active material content ranging from 0.2% to 8% by weight, preferably from 0.4% to 6% by weight, better still from 0.5% to 6% by weight and even better still from 0.8% to 5% by weight relative to the total weight of the composition.

Among the fatty alcohols, mention may be made of:
  cetyl alcohol, for instance the commercial products Cetanol from the company Kokyu Alcohol Kogyo Co., Ltd and Alfol 16 Alcohol® from the company Sasol Germany GmbH (Hamburg)
  stearyl alcohol, for instance the commercial product Kalcol 80-98® from Kao,
  arachidyl alcohol, for instance the commercial products Hainol 20SS® from the company Kokyu Alcohol Kogyo Co. Ltd and Nacol 20-95® from the company Sasol Germany GmbH (Hamburg),
  behenyl alcohol, for instance the commercial products Nacol 22-97® and Nacol 22-98® from the company Sasol Germany GmbH (Hamburg)
  and mixtures thereof.

Mention may also be made of mixtures of cetyl alcohol and stearyl alcohol, such as the commercial product Nafol 1618 ENO (Sasol Germany GmbH, Hamburg).

Oily Phase

For the purposes of the invention, the term "oily phase" means a phase comprising at least one oil and all of the lipophilic ingredients and the fatty substances used for the formulation of the compositions of the invention.

In accordance with the present invention, the oily phase comprises at least one apolar non-volatile hydrocarbon-based oil and at least one pasty apolar lipophilic hydrocarbon-based compound.

The oily phase of the emulsions is preferably present in a composition of the invention in a content ranging from 1% to 40% by weight and in particular from 10% to 30% by weight relative to the total weight of the said composition.

The apolar non-volatile hydrocarbon-based compound(s) consisting of the mixture of apolar non-volatile hydrocarbon-based oil(s) and of pasty lipophilic hydrocarbon-based compound(s) advantageously represent from 6% to 20% by weight, more preferentially from 6% to 25% by weight and even more preferentially from 13% to 40% by weight relative to the total weight of the composition.

The term "lipophilic apolar hydrocarbon-based compound" means any apolar hydrocarbon-based compound that can be fully dissolved in molecular form in an oily phase or that can be dissolved in colloidal form (for example in micellar form) in an oily phase.

The term "oil" means any fatty substance that is in liquid form at room temperature (20-25° C.) and at atmospheric pressure (760 mmHg).

For the purposes of the present invention, the term "pasty apolar lipophilic hydrocarbon-based compound" means an apolar lipophilic hydrocarbon-based compound that undergoes a reversible solid/liquid change of state, having in the solid state an anisotropic crystal organization, and comprising, at a temperature of 23° C., a liquid fraction and a solid fraction.

For the purposes of the present invention, the term "apolar lipophilic hydrocarbon-based compound" means a lipophilic hydrocarbon-based compound whose solubility parameter at 25° C., δa, is equal to 0 $(J/cm^3)^{1/2}$.

The definition and calculation of the solubility parameters in the Hansen three-dimensional solubility space are described in the article by C. M. Hansen: *The three-dimensional solubility parameters*, J. Paint Technol. 39, 105 (1967).

According to this Hansen space:
  δD characterizes the London dispersion forces derived from the formation of dipoles induced during molecular impacts;
  δp characterizes the Debye interaction forces between permanent dipoles and also the Keesom interaction forces between induced dipoles and permanent dipoles;
  δh characterizes the specific interaction forces (such as hydrogen bonding, acid/base, donor/acceptor, etc.); and
  δa is determined by the equation: $δa=(δp^2+δh^2)^{1/2}$ The parameters δp, δh, δD and δa are expressed in $(J/cm^3)^{1/2}$.

Preferentially, the apolar lipophilic hydrocarbon-based compounds according to the invention have a surface tension of less than or equal to 10 mN/m at 25° C. and at atmospheric pressure.

The surface activity is measured by static tensiometry using the Du Noüy ring.

The principle of the measurement is as follows (measurement carried out at 25° C., at atmospheric pressure):

The weight of the ring is neutralized by a tare. The ring is completely immersed in the liquid to be evaluated, then withdrawn very slowly until the force reaches its maximum. From this maximum force $F_{max}$, the surface tension is calculated according to the equation:

$$σ=F_{max}/4πR\, f_{corr}(r;R,ρ)$$

with $f_{corr}$: correction factor of the ring depending on the geometry of the ring and the density ρ. The parameters r and R respectively denote the internal and external radii of the ring.

The term "hydrocarbon-based compound" means an organic compound predominantly consisting of carbon and hydrogen atoms and more particularly free of heteroatoms. The term "heteroatom" means an atom other than carbon or hydrogen.

The term "non-volatile apolar lipophilic hydrocarbon-based compound" means any apolar lipophilic hydrocarbon-based compound whose vapor pressure at room temperature and atmospheric pressure is non-zero and less than 0.02 mmHg and better still less than $10^{-3}$ mmHg.

a) Non-Volatile Apolar Hydrocarbon-Based Oils

Examples of apolar non-volatile hydrocarbon-based oils that may be mentioned include:
  hydrocarbon-based oils, for instance squalene, linear or branched hydrocarbons derived from petroleum, such as liquid paraffin, liquid petroleum jelly and naphthalene oil, hydrogenated or partially hydrogenated polyisobutene, squalane, decene/butene copolymers and polybutene/polyisobutene copolymers, especially Indopol L-14, and polydecenes such as Puresyn 10, and mixtures thereof.

Use will be made more particularly of mixtures of hydrocarbons derived from petroleum, for instance liquid paraffin, also known under the INCI name: mineral oil or liquid petroleum jelly, such as the commercial products sold under the trade names Marcol 82® and Marcol N 82® by the company ExxonMobil Chemical and Blandol® by the company Sonneborn.

b) Pasty Apolar Hydrocarbon-Based Compounds

As examples of pasty apolar hydrocarbon-based compounds, mention may be made of the pasty linear or branched hydrocarbons derived from petroleum known under the INCI name: petrolatum, especially mineral jelly, white petrolatum, yellow petrolatum.

Use will be made more preferentially of the white petrolatum, also known under the name petroleum jelly, such as the commercial product sold under the name White Fonoline H® by the company Sonneborn.

According to a particularly preferred form of the invention, the oily phase of the compositions of the invention comprises a mixture of at least one apolar non-volatile hydrocarbon-based oil and of at least one apolar hydrocarbon-based compound and more particularly a mixture of liquid paraffin (or mineral oil) and of petrolatum and even more particularly a mixture of liquid paraffin (or mineral oil) and of white petrolatum.

c) Additional Lipophilic Compounds

According to a particular form of the invention, the oily phase may also comprise other additional lipophilic compounds.

Among these additional lipophilic compounds, mention may be made of oils or non-volatile polar pasty compounds.

Non-Volatile Polar Lipophilic Compounds

The terms "polar oil" and "polar pasty substance" mean any lipophilic compound having, at 25° C., a solubility parameter δd characteristic of dispersive interactions of greater than 16 and a solubility parameter δp characteristic of polar interactions strictly greater than 0. The solubility parameters δd and δp are defined according to the Hansen classification.

The definition and calculation of the solubility parameters in the Hansen three-dimensional solubility space are described in the article by C. M. Hansen: *The three-dimensional solubility parameters*, J. Paint Technol. 39, 105 (1967).

According to this Hansen space:
  δD characterizes the London dispersion forces derived from the formation of dipoles induced during molecular impacts;
  δp characterizes the Debye interaction forces between permanent dipoles and also the Keesom interaction forces between induced dipoles and permanent dipoles;
  δh characterizes the specific interaction forces (such as hydrogen bonding, acid/base, donor/acceptor, etc.); and
  δa is determined by the equation: $δa=(δp^2+δh^2)^{1/2}$.

The parameters δp, δh, δD and δa are expressed in $(J/cm^3)^{1/2}$.

Preferentially, the lipophilic polar compound(s) according to the invention have a surface tension of greater than 10 mN/m at 25° C. and at atmospheric pressure.

The surface activity is measured by static tensiometry using the Du Noüy ring according to the same method indicated previously.

The lipophilic polar compounds are preferably hydrocarbon-based.

The term "polar lipophilic hydrocarbon-based compound" means a polar lipophilic compound formed essentially from, or even consisting of, carbon and hydrogen atoms, and optionally oxygen and nitrogen atoms, and not containing any silicon or fluorine atoms. It may contain alcohol, ester, ether, carboxylic acid, amine and/or amide groups.

Among the polar lipophilic hydrocarbon-based compounds, mention may be made of:

phytostearyl esters, such as phytostearyl oleate, phytostearyl isostearate and triglycerides consisting of fatty acid esters of glycerol, in particular in which the fatty acids may have chain lengths ranging from $C_4$ to $C_{36}$ and especially from $C_{15}$ to $C_{36}$, these oils possibly being linear or branched, and saturated or unsaturated.

plant oils or plant butters such as wheatgerm oil, sunflower oil, grapeseed oil, sesame oil (820.6 g/mol), corn oil, apricot oil, castor oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion flower oil or musk rose oil; shea butter; cocoa butter; liquid fractions of shea butter known under the INCI name Butyrospermum parkii (shea) butter, or caprylic/capric acid triglycerides such as those sold by the company Stéarineries Dubois or those sold under the names Miglyol 810®, 812® and 818® by the company Dynamit Nobel;

synthetic ethers containing from 10 to 40 carbon atoms, such as dicaprylyl ether;

hydrocarbon-based esters of formula RCOOR' in which RCOO represents a carboxylic acid residue comprising from 2 to 40 carbon atoms, and R' represents a hydrocarbon-based chain containing from 1 to 40 carbon atoms, such as cetostearyl octanoate, isopropyl alcohol esters, such as isopropyl myristate or isopropyl palmitate, ethyl palmitate, 2-ethylhexyl palmitate, isopropyl stearate or isostearate, isostearyl isostearate, octyl stearate, diisopropyl adipate, heptanoates, and especially isostearyl heptanoate, alcohol or polyalcohol octanoates, decanoates or ricinoleates, for instance propylene glycol dioctanoate, cetyl octanoate, tridecyl octanoate, 2-ethylhexyl 4-diheptanoate and palmitate, alkyl benzoate, polyethylene glycol diheptanoate, propylene glycol 2-diethyl hexanoate, and mixtures thereof, C12 to C15 alcohol benzoates, hexyl laurate, neopentanoic acid esters, for instance isodecyl neopentanoate, isotridecyl neopentanoate, isostearyl neopentanoate and 2-octyldodecyl neopentanoate, isononanoic acid esters, for instance isononyl isononanoate, isotridecyl isononanoate and octyl isononanoate, oleyl erucate, isopropyl lauroyl sarcosinate, diisopropyl sebacate, isocetyl stearate, isodecyl neopentanoate, isostearyl behenate, and myristyl myristate;

polyol esters and pentaerythritol esters, for instance dipentaerythritol tetrahydroxystearate/tetraisostearate;

fatty alcohols containing from 12 to 26 carbon atoms, for instance octyldodecanol, 2-butyloctanol, 2-hexyldecanol, 2-undecylpentadecanol and oleyl alcohol;

higher $C_{12}$-$C_{22}$ fatty acids, such as oleic acid, linoleic acid and linolenic acid, and mixtures thereof;

fluoro oils that are optionally partially hydrocarbon-based and/or silicone-based;

fatty acids containing from 12 to 26 carbon atoms, for instance oleic acid;

dialkyl carbonates, the two alkyl chains possibly being identical or different, such as dicaprylyl carbonate sold under the name Cetiol CC® by Cognis;

non-volatile oils of high molecular mass, for example between 400 and 10 000 g/mol and in particular 650 to 10 000 g/mol, for instance linear fatty acid esters with a total carbon number ranging from 35 to 70, such as pentaerythrityl tetrapelargonate (MW=697.05 g/mol); hydroxylated esters such as polyglyceryl-2 triisostearate (MW=965.58 g/mol), and mixtures thereof.

The additional polar lipophilic compound(s) advantageously represent from 0.5% to 20% by weight relative to the total weight of the composition, more preferentially from 1% to 15% by weight and even more preferentially from 2% to 6% by weight relative to the total weight of the composition.

Among the additional polar lipophilic compounds, use will be made more preferentially of plant oils or plant butters and even more particularly of the liquid fractions of shea butter (INCI name: Butyrospermum parkii (shea) butter).

Among these additional lipophilic compounds, mention may also be made of volatile or non-volatile silicone oils; volatile or non-volatile fluoro oils; waxes; silicone gums such as dimethiconol, and mixtures thereof.

For the purposes of the present invention, the term "silicone oil or gum" means an oil or gum comprising at least one silicon atom, and in particular at least one Si—O group.

The term "fluoro oil" is intended to mean an oil comprising at least one fluorine atom.

Silicone Oils

The non-volatile silicone oils may be chosen in particular from non-volatile polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy)diphenylsiloxanes, diphenyl dimethicones, diphenyl(methyldiphenyl)trisiloxanes or (2-phenylethyl)trimethylsiloxysilicates.

Examples of volatile silicone oils that may be mentioned include volatile linear or cyclic silicone oils, in particular those with a viscosity≤8 centistokes ($8 \times 10^{-6}$ m$^2$/s) and in particular containing from 2 to 7 silicon atoms, these silicones optionally comprising alkyl or alkoxy groups containing from 1 to 10 carbon atoms. As volatile silicone oil that may be used in the invention, mention may be made in particular of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Mention may also be made of volatile linear alkyltrisiloxane oils of general formula (I):

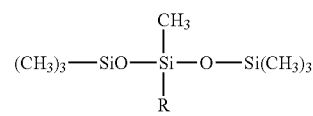

where R represents an alkyl group comprising from 2 to 4 carbon atoms, one or more hydrogen atoms of which can be replaced by a fluorine or chlorine atom.

Mention may be made, among the oils of general formula (I), of:
3-butyl-1,1,1,3,5,5,5-heptamethyltrisiloxane,
3-propyl-1,1,1,3,5,5,5-heptamethyltrisiloxane, and
3-ethyl-1,1,1,3,5,5,5-heptamethyltrisiloxane,
corresponding to the oils of formula (I) for which R is, respectively, a butyl group, a propyl group or an ethyl group.

Fluoro Oils

Use may also be made of volatile fluoro oils, such as nonafluoromethoxybutane, decafluoropentane, tetradecafluorohexane, dodecafluoropentane, and mixtures thereof.

Waxes

The wax is in general a lipophilic compound that is solid at room temperature (25° C.), with a reversible solid/liquid change in state, having a melting point of greater than or equal to 30° C., which may be up to 200° C. and in particular up to 120° C.

Among the waxes, mention may be made of beeswax, carnauba or candelilla wax, paraffin waxes, lignite waxes, microcrystalline waxes, ceresin or ozokerite, or synthetic waxes, such as polyethylene waxes or Fischer-Tropsch waxes.

Hydrophilic Gelling Polysaccharides

The term "polysaccharide" means any polymer consisting of several saccharides (or monosaccharides) having the general formula:

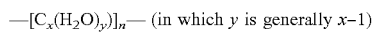

—[C$_x$(H$_2$O)$_y$)]$_n$— (in which $y$ is generally $x-1$)

and linked together via O-oside bonds.

For the purposes of the present invention, the term "hydrophilic gelling polysaccharide" means any water-soluble or water-dispersible polysaccharide that is capable of giving a gelled solution after implementation with or without heating.

In general, polysaccharides may be divided into several categories.

Thus, polysaccharides that are suitable for use in the invention may be homopolysaccharides such as fructans, glucans, galactans and mannans or heteropolysaccharides such as hemicellulose.

Similarly, they may be linear polysaccharides such as pullulan or branched polysaccharides such as gum arabic and amylopectin, or mixed polysaccharides such as starch.

More particularly, the polysaccharides that are suitable for use in the invention may be distinguished according to whether or not they are starchy.

In general, the starchy polysaccharides are preferably chosen from starches.

In general, the non-starchy polysaccharides may be chosen from polysaccharides produced by microorganisms; polysaccharides isolated from algae, and higher plant polysaccharides, such as homogeneous polysaccharides, in particular celluloses and derivatives thereof or fructosans, heterogeneous polysaccharides such as gum arabics, galactomannans, glucomannans and pectins, and derivatives thereof.

In particular, the non-starchy polysaccharides may be chosen from fructans, gellans, glucans, amylose, amylopectin, glycogen, pullulan, dextrans, celluloses and derivatives thereof, in particular methylcelluloses, hydroxyalkylcelluloses, ethylhydroxyethylcelluloses and carboxymethylcelluloses, mannans, xylans, lignins, arabans, galactans, galacturonans, alginate-based compounds, chitin, chitosans, glucuronoxylans, arabinoxylans, xyloglucans, glucomannans, pectic acids and pectins, arabinogalactans, carrageenans, agars, glycosaminoglycans, gum arabics, tragacanth gums, ghatti gums, karaya gums, locust bean gums, galactomannans such as guar gums and nonionic derivatives thereof, in particular hydroxypropyl guar, and ionic derivatives thereof, biopolysaccharide gums of microbial origin, in particular scleroglucan or xanthan gums, mucopolysaccharides, and in particular chondroitin sulfates, and mixtures thereof.

Starches are preferentially used.

Preferentially, the hydrophilic gelling polysaccharide(s) are present in contents ranging from 0.5% to 8% by weight and more preferentially from 1% to 5% by weight relative to the total weight of the composition.

Hydrophilic Gelling Starches

The hydrophilic gelling starches that may be used in the present invention are more particularly macromolecules in the form of polymers formed from elemental units that are anhydroglucose units. The number of these units and their assembly make it possible to distinguish amylose (linear polymer) and amylopectin (branched polymer). The relative proportions of amylose and of amylopectin, and their degree of polymerization, vary as a function of the botanical origin of the starches. The amylose/amylopectin weight ratio may range from 30/70 (corn) to 16/84 (rice). The molecular weight of the amylose is preferably up to 1 million by weight and that of the amylopectin is preferably from 100 to 500 million by weight.

The starch molecules used in the present invention may be unmodified or chemically or physically modified.

Their botanical origin may be cereals or tubers. Thus, the natural starches may be chosen from corn starch, rice starch, tapioca starch, cassava starch, barley starch, potato starch, wheat starch, sorghum starch, palm starch and pea starch.

Among the unmodified starches, mention may be made of unmodified corn starches (INCI name: *Zea mays* starch), for instance the products sold under the trade name Farmal CS®, in particular the commercial product Farmal CS 3650® from the company Corn Products International.

Mention may also be made of unmodified rice starches (INCI name: *Oryza sativa* (rice) starch), for instance the commercial product Remy DR I® sold by the company Beneo-Remy.

According to a particular form of the invention, the starches used are modified by crosslinking with functional agents capable of reacting with the hydroxyl groups of the starch molecules, which will thus bond together (for example with glyceryl and/or phosphate groups).

Monostarch phosphates (of the type st-O—PO—(OX)$_2$), distarch phosphates (of the type st-O—PO—(OX)—O-st) or even tristarch phosphates (of the type St-O—PO—(O-St)$_2$) or mixtures thereof may especially be obtained by cross-linking with phosphorus compounds.

Use will preferentially be made of distarch phosphates or compounds rich in distarch phosphate, in particular the hydroxypropyl ethers of distarch phosphate having the INCI name: Hydroxypropyl Starch Phosphate, for instance the products sold under the trade names Farinex VA70 C or Farmal MS 689 ® from the company AVEBE Stadex; or the products sold under the trade names Structure BTC®, Structure HVS®, Structure XL® or Structure *Zea*® from National Starch (corn distarch phosphate).

Even more preferentially, the starch will be chosen from corn distarch phosphates or compounds rich in corn distarch phosphate, in particular corn distarch phosphate hydroxypropyl ethers.

Preferentially, the hydrophilic gelling starch(es) are present in contents of greater than 1% by weight, more preferentially ranging from 2% to 6% by weight and even more preferentially from 3% to 5% by weight relative to the total weight of the composition.

Galenical Forms

The compositions according to the invention are oil-in-water emulsions. They are generally in the form of a lotion, a milk or a cream.

The compositions of the invention in the form of an oil-in-water emulsion are obtained according to standard manufacturing processes. They may especially be obtained via a one-pot process in a tank, comprising emulsification of the aqueous and oily phases with heating so as to melt the lipophilic compounds, addition of the hydrophilic gelling polysaccharide, gelation with heating (especially to 70° C. for the formation of a starch paste), and then dilution.

Another process, by concentrated dilution, may also be performed for obtaining a glossy, fine white emulsion, the starch paste having been prepared beforehand with heating.

They may be packaged, for example, in tubes, bottles or pump-dispensing bottles, or in single-dose sachets.

Additives

The cosmetic compositions according to the invention may contain additives that are common in cosmetics: pigments, dyes, biological active agents (anti-ageing, anti-greasy skin, lightening, bleaching, antioxidants, etc.), sunscreens, sequestrants, moisturizers, softeners, polymers, vitamins, preserving agents, or other cosmetic excipients.

Concrete, but in no way limiting, examples illustrating the invention will now be given.

In the examples, all the percentages are given on a weight basis, unless otherwise indicated, the temperature is in degrees Celsius, unless otherwise indicated, and the pressure is atmospheric pressure, unless otherwise indicated. In the examples, the amounts of the composition ingredients are given as weight percentages relative to the total weight of the composition.

EXAMPLES

Examples 1 to 5

| Ingredients | Example 1 (invention) | Example 2 (outside the invention) | Example 3 (outside the invention) |
|---|---|---|---|
| White petrolatum (White Fonoline H ® - Sonneborn) | 13 | 13 | 13 |
| Liquid paraffin (Blandol ® - Sonneborn) | 6.5 | 6.5 | 6.5 |
| *Butyrospermum parkii* (shea) butter | 0.5 | 0.5 | 0.5 |
| Cetearyl alcohol mixture (Nafol 1618 EN ® - Sasol Germany GmbH Hamburg) | 2 | 2 | 2 |
| Ethylenediaminedisuccinic acid, trisodium salt, as an aqueous 30% solution | 0.5 | 0.5 | 0.5 |
| Hydroxypropyl starch phosphate (Structure Zea ® - National Starch) | 4 | 4 | — |
| Sodium polyacrylate (Cosmedia SP ® - Cognis) | — | — | 4 |
| Monoglyceryl stearate/ PEG-100 stearate mixture (Arlacel 165 ® - Croda) | 2 | — | 2 |
| Polysorbate-60 (Tween 60 SS-(TH) ® - Croda) | — | 2 | — |
| Glycerol | 1 | 1 | 1 |
| Fragrance | 1 | 1 | 1 |
| Preserving agents | qs | qs | qs |
| Water | qs 100 | qs 100 | qs 100 |

Formulations 1 to 3 were obtained via a one-pot process in a tank, comprising emulsification of the aqueous and oily phases with heating so as to melt the lipophilic compounds, addition of the hydrophilic gelling polysaccharide, gelation at 70° C. (formation of a starch paste), and then dilution.

Example 4 (Outside the Invention)

corresponds to the commercial product Olay Body®—"Quench In-Shower Body Lotion" comprising the following ingredients: water, petrolatum, mineral oil, hydroxypropyl starch phosphate, fragrance, stearyl alcohol, mica, polysorbate 60, titanium dioxide, DMDM hydantoin, cetyl alcohol, triethoxycaprylylsilane, disodium EDTA, phenoxyethanol iodopropynyl butylcarbamate, tin oxide.

Example 5 (Outside the Invention)

corresponds to the commercial product Nivea®—"Under The Shower Body Balm Nutritive" comprising the following ingredients: water, microcrystalline wax, liquid paraffin, glycerol, cetearyl alcohol, hydrogenated cocoyl glycerides, stearyl alcohol, myristyl alcohol, sea salt, sodium carbomer, sodium acrylates/C10-30 alkyl acrylate crosspolymer, aluminium starch octenylsuccinate, phenoxyethanol, methylisothiazolinone, linalool, limonene, butylphenyl methylpropional.

Test of Deposition on Wet Skin

For each of the formulations 1 to 5, a test was performed for the measurement of the deposition of the product on wet skin rinsed with water according to the following protocol;

Reconstructed skins of the type Skin FX® with a surface area of 76.14 cm$^2$ (SH H40 BAK CST-Atelier 69) were used, which were placed in an oven at 37° C.

The Skin FX® skins were weighed on a precision balance (Mettler Toledo XP504®).

Each tested reconstructed skin was applied to the hand.

The hands and the reconstructed skin were moistened with water at 38° C.

1 g of each product was applied to each tested reconstructed skin.

Each product was spread in the hand, rubbing to and fro 15 times.

Each treated skin was passed under tap water (flow rate of 2 L/minute and controlled temperature of 38° C.) for 5 seconds, and the "rinsed skin" sensation was observed.

The treated reconstructed skin was then dried for 35 minutes in an oven at 37° C.

The dried skin was weighed, and the weight gain was calculated to quantify the deposition of film on the skin.

The amount of product deposited is expressed in mg/cm$^2$. The average deposition of product on 3 measurements was determined for each Example 1 to 5.

According to this test, the deposition of product is estimated as being

Perceptible and sparingly tacky when the deposit is from 0.15 to 0.4 mg/cm$^2$

Insufficiently perceptible when the deposit is less than 0.1 mg/cm$^2$

Too thick and tacky when the deposit is greater than 0.4 mg/cm$^2$

The results obtained are indicated in the following table:

| Composition | Ex. 1 (invention) | Ex. 2 (outside the invention) | Ex. 3 (outside the invention) | Ex. 4 (outside the invention) | Ex. 5 (outside the invention) |
|---|---|---|---|---|---|
| Average deposit | 0.165 ± 0.005 | 0.039 ± 0.04 | 1.069 ± 0.04 | 0.632 ± 0.05 | 0.646 ± 0.09 |

It was observed that composition 1 according to the invention comprising the monoglyceryl stearate/PEG-100 stearate emulsifying mixture leads to a perceptible and sparingly tacky deposit, unlike composition 2 comprising as emulsifier Polysorbate-60 at the same concentration (2% by weight), which gives an insufficiently perceptible deposit.

It was observed that composition 1 according to the invention comprising the gelling agent hydroxypropyl starch phosphate led to a perceptible and sparingly tacky deposit, unlike composition 3 comprising as gelling agent sodium polyacrylate, which gives an excessively thick and tacky deposit comparable to a standard body milk applied dry.

It was observed that composition 1 according to the invention led to a perceptible and sparingly tacky deposit, unlike compositions 4 and 5, which give an excessively thick and tacky deposit comparable to a standard body milk applied dry.

After application, composition 1 according to the invention leaves a soft, sparingly greasy and sparingly tacky deposit, which makes it possible firstly to get dressed quickly and secondly a significant gain in moisturization after 24 hours. Furthermore, it is stable on storage especially after 2 months at a temperature of 45° C. (absence of phase separation, of drop in pH and of loss of viscosity).

Gain in Moisturization of Composition 1 According to the Invention

A moisturization test was also performed on composition 1 according to the following protocol.

Number of subjects: 24 Caucasian women, from 18 to 65 years old

Nature of skin: dry skin of the leg (outer side) (electrical capacity of 20 to 40)

Methodology:

Humidity rate 45±5% and temperature 21±1° C.

Zones studied: right and/or left leg (outer side) at random; treated zones and control zones Measurement with a CM825® (Courage and Khasaza) corneometer of the electrical capacity.

Kinetics; T0 (baseline), T8h and T24h after application

Statistics: Student test or Wilcoxon test ($p<0.05$) according to the normality of the distributions The electrical characteristics of the stratum corneum depend on the amount of water. The measurements of the electrical capacity are taken using a corneometer. The values given on a scale of arbitrary units from 0 to 130 show the degree of moisturization of the upper layers of the epidermis at a given time.

The gain in moisturization (expressed as a percentage) on the upper layers of the epidermis for a test product is determined by calculating the percentage of variation in electrical capacity at $T_x$ (x being the time) in comparison with the initial values and those for the control zone, starting with the mean values according to the following equation Mean gain in moisturization=$[(T_x-T_0/T_0) \times 100]_{treated} - [(T_x-T_0/T_0) \times 100]_{control}$

| Mean gain in moisturization | Composition 1 (invention) | Significance |
|---|---|---|
| After 30 minutes | +8.6 | $p < 0.05$ |
| After 8 hours | +8.9 | $p < 0.05$ |
| After 24 hours | +6.7 | $p < 0.05$ |

Conclusion:

It was found that formulation 1 produced a statistically significant gain in moisturization at T30 min, T8H and T24H.

Example 6 (Outside the Invention)

| Ingredients | Example 6 |
|---|---|
| White petrolatum (White Fonoline H® - Sonneborn) | 13 |
| Liquid paraffin (Blandol® - Sonneborn) | 6.5 |
| *Butyrospermum parkii* (shea) butter | 0.5 |
| Ethylenediaminedisuccinic acid, trisodium salt, as an aqueous 30% solution | 0.2 |
| Cetearyl alcohol mixture (Nafol 1618 EN® - Sasol Germany GmbH Hamburg) | 2.8 |
| Hydroxypropyl starch phosphate (Structure Zea® - National Starch) | 3.5 |
| Polysorbate-60 | 0.5 |
| Glycerol | 1 |
| Fragrance | 1 |
| Preserving agents | qs |
| Water | qs 100 |

Composition 6 was prepared under the same conditions as Examples 1 to 3.

It was observed that composition 6 comprising Polysorbate-60 as emulsifying surfactant was unstable on storage after 2 months at room temperature and at 45° C., which was reflected by a loss of viscosity and a drop in pH.

Examples 7 and 8 (Invention)

| Ingredients | Example 7 (invention) | Example 8 (invention) |
|---|---|---|
| White petrolatum (White Fonoline H® - Sonneborn) | 15 | 15 |
| Liquid paraffin (Blandol® - Sonneborn) | 7 | 7 |

| Ingredients | Example 7 (invention) | Example 8 (invention) |
|---|---|---|
| *Butyrospermum parkii* (shea) butter | 3 | 3 |
| Ethylenediaminedisuccinic acid, trisodium salt, as an aqueous 30% solution | 0.2 | 0.2 |
| Cetearyl alcohol mixture (Nafol 1618 EN ® - Sasol Germany GmbH Hamburg) | 2 | 2 |
| Hydroxypropyl starch phosphate (Structure Zea ® - National Starch) | 4 | 4 |
| Monoglyceryl stearate/PEG-100 stearate mixture (Arlacel 165 ® - Croda) | 2 | 2 |
| Glycerol | 1 | 3 |
| Fragrance | 1 | 1 |
| Preserving agents | qs | qs |
| Water | qs 100 | qs 100 |

Compositions 7 and 8 were prepared under the same conditions as Examples 1 to 3. After application to wet, rinsed and wiped skin, they leave a water-resistant film, which has a soft, sparingly tacky and sparingly greasy feel, and, after 24 hours, give a sensation of well-moisturized skin. The compositions are stable on storage after 2 months at room temperature and at 45° C.

The invention claimed is:

1. A composition in the form of an oil-in-water emulsion comprising, in a physiologically acceptable medium:
   a) at least one aqueous phase in an amount ranging from 30% to 70% by weight based upon the total weight of the composition; and
   b) at least one oily phase in an amount ranging from 1% to 40% by weight based upon the total weight of the composition and comprising at least one apolar non-volatile hydrocarbon-based oil and at least one pasty apolar lipophilic hydrocarbon-based compound; and
   c) at least one hydrophilic gelling polysaccharide in an amount ranging from 0.5% to 8% by weight based upon the total weight of the composition; and
   d) at least one mixture of emulsifying nonionic surfactants in an active material amount ranging from 0.2% to 6% by weight based upon the total weight of the composition and comprising (i) at least one fatty acid ester of a $C_8$-$C_{24}$ fatty acid and a polyol selected from the group consisting of glycerol, polyglycerol, sorbitan and mixtures thereof and (ii) at least one polyalkylene glycol ester of a polyalkylene glycol and a $C_{18}$-$C_{24}$ fatty acid.

2. The composition according to claim 1, wherein:
   the aqueous phase is present in a content ranging from 32% to 60% by weight relative to the total weight of the said composition and
   the oily phase is present in a content ranging from 10% to 30% by weight relative to the total weight of the said composition.

3. The composition according to claim 1, wherein:
   the fatty acid ester of polyalkylene glycol is chosen from esters formed from 1 to 100 ethylene oxide units and from at least one fatty acid chain comprising from 12 to 22 carbon atoms and
   the fatty acid ester of polyol is chosen from esters of glycerol or of polyglycerol and of a $C_8$-$C_{24}$ fatty acid.

4. The composition according to claim 1, wherein the mixture of nonionic surfactants is a mixture of glyceryl monostearate and PEG-100 stearate.

5. The composition according to claim 1, wherein the mixture of nonionic surfactants is present in an active material content ranging from 0.4% to 5% by weight relative to the total weight of the composition.

6. The composition according to claim 1, which comprises at least one additional emulsifying surfactant.

7. The composition according claim 1, wherein the mixture of apolar hydrocarbon-based oil(s) and of pasty lipophilic hydrocarbon-based compound(s) represents from 6% to 20% by weight relative to the total weight of the composition.

8. The composition according to claim 1, wherein:
   the apolar non-volatile hydrocarbon-based oils are chosen from mixtures of hydrocarbons derived from petroleum, and
   the pasty apolar hydrocarbon-based compounds are chosen from mixtures of hydrocarbons derived from petroleum.

9. The composition according to claim 1, wherein the oily phase comprises a mixture of liquid paraffin (or mineral oil) and of petrolatum.

10. The composition according to claim 1, wherein the oily phase also comprises a non-volatile polar hydrocarbon-based oil.

11. The composition according to claim 1, wherein the gelling polysaccharide is chosen from starchy polysaccharides.

12. The composition according to claim 11, in which the starch is chosen from distarch phosphates or compounds rich in distarch phosphate.

13. The composition according to claim 12, in which the starch is chosen from corn distarch phosphates and compounds rich in corn distarch phosphate.

14. The composition according to claim 11, in which the hydrophilic gelling starch(es) are present in contents of greater than 1% by weight relative to the total weight of the composition.

15. The composition according to claim 1, in the form of a lotion, milk or cream.

16. A cosmetic care process for moisturizing a human keratin material, in particular the skin, wherein it comprises the application to the surface of the said keratin material of a composition as defined in claim 1.

17. The process according to claim 16, wherein the composition is applied to the surface of the human keratin material on contact with water, the said process then comprising rinsing with water and wiping of the said keratin material.

18. The composition according to claim 2, wherein:
   the fatty acid ester of polyalkylene glycol is chosen from esters formed from 1 to 100 ethylene oxide units and from at least one fatty acid chain comprising from 12 to 22 carbon atoms and
   the fatty acid ester of polyol is chosen from esters of glycerol or of polyglycerol and of a $C_8$-$C_{24}$.

19. The composition according to claim 2, wherein the mixture of nonionic surfactants is a mixture of glyceryl monostearate and PEG-100 stearate.

20. The composition according to claim 3, wherein the mixture of nonionic surfactants is a mixture of glyceryl monostearate and PEG-100 stearate.

* * * * *